Figure 1:
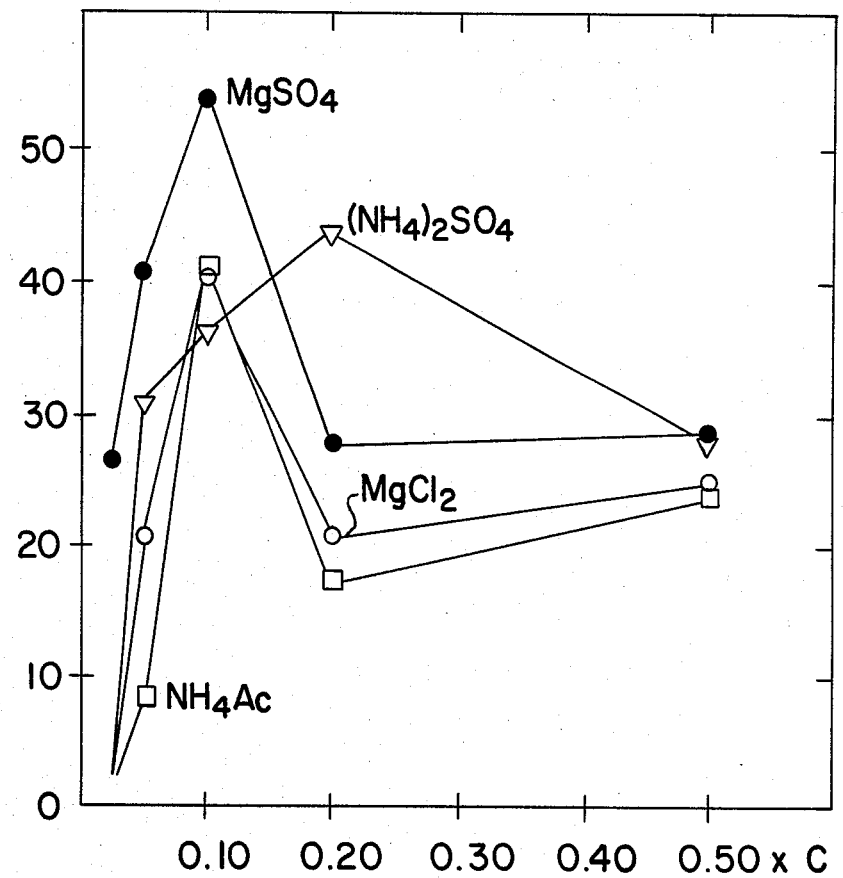

United States Patent [19]

Kjelleberg et al.

[11] Patent Number: 4,581,227

[45] Date of Patent: Apr. 8, 1986

[54] CONTROL OF MICROFLORA

[76] Inventors: Staffan Kjelleberg, Södra Vägen 79, S-412 54 Göteborg; Peter Rönnow, Violinvägen 36, S-435 00 Mölnlycke, both of Sweden

[21] Appl. No.: 613,772

[22] PCT Filed: Oct. 6, 1983

[86] PCT No.: PCT/SE83/00348

§ 371 Date: May 15, 1984

§ 102(e) Date: May 15, 1984

[87] PCT Pub. No.: WO84/01713

PCT Pub. Date: May 10, 1984

[30] Foreign Application Priority Data

Nov. 3, 1982 [SE] Sweden ............................ 8206250

[51] Int. Cl.[4] ............... A61K 33/00; A61K 33/06; A61K 31/12; A61K 31/35

[52] U.S. Cl. .................................... 424/49; 424/54; 424/58; 424/153; 424/154; 424/166; 514/474

[58] Field of Search ............... 424/49, 54, 58, 153, 424/154, 166, 280; 574/474

[56] References Cited

U.S. PATENT DOCUMENTS

| | | | |
|---|---|---|---|
| 3,932,603 | 1/1976 | Haas | 424/49 |
| 4,229,430 | 10/1980 | Fahim et al. | 424/49 |
| 4,327,079 | 4/1982 | Aoki | 424/49 |
| 4,446,125 | 5/1984 | Mookherjee et al. | 424/49 |
| 4,457,909 | 7/1984 | Tamés | 424/153 |

OTHER PUBLICATIONS

Chem. Abstracts vol. 95, 86325t, Sunstar Inc., 1981, p. 342.
Chem. Abstracts vol. 92, 88520c, Shankar et al., 1980, p. 93.
Chem. Abstracts vol. 92, 82452k, Ghatak, 1980 p. 391.
Hackh's Chemical Dictionary, McGraw-Hill Book Co., 1972 p. 190.

Primary Examiner—John Kight
Assistant Examiner—Nathan M. Nutter
Attorney, Agent, or Firm—Dennison, Meserole, Pollack & Scheiner

[57] ABSTRACT

The present invention relates to a method of controlling microorganisms adhering to the surfaces of biological material, by the administration of substances which alter the water-structure binding capacity of the surfaces and phase-boundaries.

Organic and inorganic salts, erythrosine or anti-oxidants are used to remove micro-organisms from the surfaces. Cucumine or derivatives thereof are used as adhesion-stimulating substances.

The invention also relates to preparations for performing the method, such as ointments, creams and bathing liquids containing the above-mentioned substances, as well as to dentifrices containing one or more organic or inorganic salts.

18 Claims, 1 Drawing Figure

CONTROL OF MICROFLORA

The present invention relates to a method of removing undesired micro-organisms, including those of pathogenic nature, attached to surfaces, phase boundaries and interfaces. The invention also relates to a method of effecting an adhesion-stimulating result for desired micro-organisms by administering adhesion-stimulating substances. The invention also relates to preparations for achieving the abovementioned results.

In the following the invention will be described first as applied to the care of livestock, other applications being dealt with afterwards.

The present invention can be used to prevent the establishment of pathogenic bacteria flora and to eliminate such flora already established in pigs, calves and poultry. By "poultry" is meant chickens, turkeys, geese and ducks, for instance.

The mortality rate of such animals is at present high as a result of the establishment and colonization of pathogenic bacteria in the stomach and intestines. Pathogenic bacteria oust the normal bacteria flora, adhere to the bonding seats on the walls of the intestines, give rise to disease symptoms such as diarrhoea and result in increased mortality. Some farms lose large numbers of animals following an outbreak of pathogenic bacteria such as *Escherichia coli, Salmonella typhimurium,* Salmonella Sp., Shigella sp. and *Clostridium perfringens.*

Current methods of reducing the risk of outbreaks of the type mentioned above can be divided into two categories:

1. Treatment with antibiotics
2. Oral administration of non-pathogenic bacteria in pure or mixed cultures There are a number of drawbacks in treating animals with antibiotics, which makes the method less attractive.

Examples are:

Non-selectivity, which also causes a reduction in the natural intestinal flora;

High cost;

The appearance of resistant strains;

It is time-consuming and impractical when the farm worker cannot be responsible for all steps of the treatment himself;

Legislative control of treatment with antibiotics.

It has been impossible to follow up successful laboratory experiments with oral administration of non-pathogenic bacteria resulting in reduced risk of diarrhoea in pigs, under full-scale conditions. Careful tests with commercial products containing, e.g. *Lactobacillus acidophilus* and *Lactobacillus bulgaricus* have not given significant positive results. Neither has it been possible to colonize the intestines of pigs with *Streptococcus faecium.* It has not been possible to establish *Lactobacillus acidophilus* in chicken intestines and there have been no successful large-scale experiments with oral administration to chickens.

More recent experiments with plasmid-carrying strains to increase adhesion appear to be futile due to instability of the plasmids and difficulties in maintaining suitable selection pressure for their preservation.

Initial studies of the adhesion of bacteria to the intestinal walls revealed surprisingly that oral administration is anyway an extremely successful method of preventing the establishment, colonization and growth of pathogenic bacteria in the stomach and intestines of pigs, calves and poultry.

The following points comprise the basis of the process forming the grounds of the present invention is based:

1. The stomach and intestines is rendered substantially bacteria-free by treating with anti-microbial substances or substances which adhere to the walls and block the adhesion of bacteria.
2. Substances are used which increase the degree of adhesion of the orally administered non-pathogenic bacteria.
3. Non-pathogenic enterobacteria are cultivated in a special way to produce specific protein-protrusions, fimbria, giving rise to greatly increased adhesion of bacteria to the bacteria surface of intestinal walls.

Substances which may be used to remove bacteria from surfaces include erythrosine, anti-oxidants, and organic or inorganic salts. Among the salts which can be used are magnesium, aluminum, ammonium, beryllium, lithium and calcium salts. The various bacteria removing substances may be used alone or in combination.

Substances which may be used to increase the degree of adhesion of the non-pathegenic bacteria include curcumin and its derivatives. Curcumin also known as 1,7-bis(4-hydroxy-3-methoxyphenyl)-1,6-heptadiene-3,5-dione is the coloring matter of tumeric, the rhizome of *curcuma longa.* Curcumin has the following structural formula:

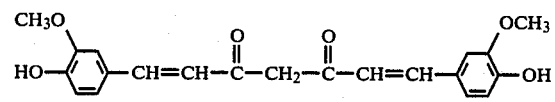

The derivatives of curcumin which may be used as adhesion promoting substances include those of the following structural formula:

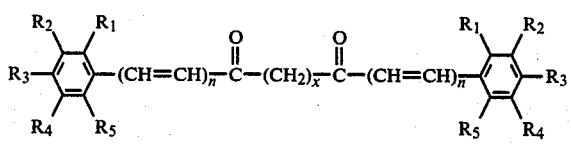

Where $N=1,2,3\ldots$, $X=1,2,3,4\ldots$, and $R_1$–$R_5$ may be same or different, and may be for example, H, OH, $OCH_3$, $OCH_2CH_3$, $CH_3$, $CH_2CH_3$, COOH, or $CH_2COOH$.

The curcumin may be administered in its pure form, or may be administered in the form of oleo-resins and/or cleaned fractions of a plant extract containing curcumin, which also includes turmeric acid.

The invention is further illustrated with reference to the following non-limiting examples of its application:

EXAMPLE 1

RELATING TO PIGS AND CALVES

A. Erythrosine, anti-oxidants or $MgSO_4$ were mixed into the fodder or drinking water in concentrations expressed in g/kg bodyweight and day 0.06, 1, 0.5, respectively. Observation of laboratory animals (mice) with a scanning transmission electron microscope has revealed that the bacterial flora in the intestines were greatly reduced. Large bacteria-free areas were observed using erythrosine and anti-oxidants and the use of MgSO₄ resulted in completely bacteria-free intestines.

B. Faeces samples from uncontaminated animals were coated with MacConkey plates. The isolated samples were tested using a screening test, for Enterobacteriaceae in order to avoid *Escherichia coli* and Salmonella types. A suitable culture was selected and cultivated to produce fimbria which were checked with the yeast agglutination method. Intestinal wall was at the same time taken with caecum and large intestine of uncontaminated animals. Irreversibly bound bacteria plus intestinal wall was homogenized and frimbria-carrying bacteria were produced as described above.

Binding studies revealed that curcumine and similar compounds increased the degree of adhesion of *Lactobacillus acidophilus* to pig intestines five times.

The following bacteria preparations were produced for oral adminstration to pigs in skimmed milk fermented with *Lactobacillus acidophilus*. Capsules (sterilized) were used containing $10^{10}$/ml *Streptococcus caecalis* or *S. faecium*, fimbriated Enterobacteria and curcumine or analogous compounds, in sizes suited to the size of the animals. Curcumine is active if administered in amounts of 0.8 g/body-weight and day. This bacteria preparation was administered immediately after the treatment described under A.

EXAMPLE 2

RELATING TO POULTRY

A and B in Example 1, with the exception of the *Lactobacillus acidophilus*. The preparation was administered in drinking water.

Stages A and B can be repeated as necessary at intervals.

Some of the mechanisms binding micro-organisms to phase boundaries or interfaces are responsible for irreversible binding which acts over short distances (2–5 nm). This results in strong adhesion which is only mechanically broken by tearing away the components belonging to the adhered micro-organisms. Hydrophobic interaction is primarily responsible for this type of irreversible binding.

Successful treatment, i.e. removal of micro-organisms adhered in this manner, is effected by modifying the quantity of substances, salts or other components, able to alter the water-structure binding properties in the surfaces, phase boundaries and interfaces of the system.

Experiments with infectious bacteria in wounds and micro-organisms adhered to teeth showed surprisingly that the principles and substances used in the experiments with livestock described above were also extremely effective in the following widely differing fields of application.

The following points constitute the basis of the process used in these new fields of application.

1. Substances altering the degree of hydrophobic interaction between surface and micro-organisms are added to the surface/phase boundaries being treated, so that smaller or larger portions of the irreversibly adhere micro-organisms become detached.

2. Substances promoting adhesion of specifically supplied micro-organisms are added to the system treated under point 1.

The procedure is further illustrated with reference to the following non-limiting examples.

EXAMPLE 3

In both model system and during clinical testing using dentifrice or mouthwash with the addition of magnesium sulphate (MgSO₄) for brushing teeth or rinsing out the mouth, a significant reduction in the number of bacteria adhered was established.

EXAMPLE 4

Bathing liquids to which magnesium sulphate and/or anti-oxidants had been added were applied to a wound. Here too a significant reduction in the number of bacteria adhered to the wound surface was noted. It was also noted that cleaning the surface of a wound in this manner stimulated healing.

The result of the method is also illustrated by but not limited to the following experiments in a model system.

A number of glass tubes, all the same size, were immersed in a suspension of bacteria marked with a radioactive isotope (tritium) and the bacteria were allowed to adhere over a period of 30 minutes. The glass tubes were then removed one by one and rinsed by repeated dipping (30 times) in a buffer solution in order to remove reversibly bound bacteria. Only the irreversibly bound bacteria then remained on the glass tube. The glass tube was then immersed in a salt solution for 5 minutes. After rinsing, the quantity of bacteria adhered to the tube was determined by measuring the radiation in a liquid scintillator.

A comparison of the various glass tubes which had been immersed in salt solution of various concentrations with control tubes which had undergone the same treatment with the exception of immersion in the salt solution, enabled assessment of the effect of the salt solution on the irreversible bound bacteria. The table below and the drawing show the effects of the various salts on detachment of the irreversibly adhered bacteria, expressed in percentage of the quantity of irreversibly adhered bacteria before the salt treatment. The concentrations of the solutions are in multiples of a specific critical concentration (C) of the basic solution.

Of the salts tested in this series of experiments, magnesium sulphate (MgSO₄) gave the strongest detaching effect. However, magnesium chloride (MgCl) and ammonium acetate (NH₄Ac) solutions also gave good results, whereas ammonium sulphate ((NH₄)₂SO₄) solutions gave a slightly different pattern.

Several other compounds and salts have been tested besides those mentioned in this series of experiments, and the results were similar.

TABLE

Detachment percentage of irreversibly adhered bacteria after treatment.
The number of bacteria irreversibly adhered to the glass tube is $3.0 \times 10^6$ before treatment.

| Salts | Salt concentration in multiples of basic solution C | | | |
|---|---|---|---|---|
| | 0.05 × C | 0.1 × C | 0.2 × C | 0.6 × C |
| MgSO₄ | 41 | 54 | 28 | 28 |
| MgCl₂ | 20 | 40 | 21 | 25 |
| NH₄ Acetate | 8.5 outline | 41 | 17 | 24 |
| (NH₄)SO₄ | 31 | 36 | 44 | 28 |

FIG. 1 shows the detachment of irreversibly adhered bacteria after treatment with salt solutions of various concentrations. The salt concentration is expressed in multiples of the basic solution C. The number of irreversibly adhered bacteria is ca. $3.0 \times 10^6$ per glass tube before treatment.

The preparations containing curcumine described in the following claims are intended for use in performing the method according to the invention, but can also be used for other purposes, such as stimulating secretion in micro-organisms tissues and tissue cells.

We claim:

1. Method for removing undesired bacteria and promoting the establishment of desired bacteria on an interfacial surface, comprising the steps of:
   (a) treating said surface with an effective amount of material which will substantially remove the bacteria attached to said surface;
   (b) applying to said treated surface an effective amount of an adhesion-promoting material comprising curcumin or a derivative thereof; and
   (c) applying to said treated surface a desired, fimbriated bacteria.

2. Method according to claim 1, wherein said surface is treated with an organic and/or inorganic salt for substantial removal of the attached bacteria.

3. Method according to claim 2, wherein said said salt is selected from the group consisting of salts of magnesium, aluminum, ammonium, beryllium, lithium, calcium, and mixtures thereof.

4. Method according to claim 1, wherein said surface is treated with erythrosine and/or an anti-oxidant for substantial removal of the attached bacteria.

5. Method according to claim 2, wherein said surface is treated with erythrosine and/or an anti-oxidant together with said salt for substantial removal of the attached bacteria.

6. Method according to claim 1, wherein said adhesion-promoting material is a derivative of curcumin of the structural formula:

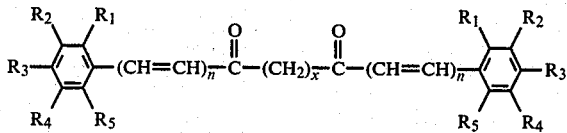

wherein n is 1, 2 or 3, x is 1, 2, 3 or 4, and $R_1$–$R_5$ are independently selected from the group consisting of H, OH, $OCH_3$, $OCH_2CH_3$, $CH_3$, $CH_2CH_3$, COOH, and $CH_2$-COOH.

7. Method according to claim 1, wherein said curcumin is applied in the form oleo-resins and/or cleaned fractions of a plant extract containing curcumin, which also includes turmeric acid.

8. Method according to claim 1, wherein said surface is a surface of the mouth, stomach, or intestine of a living animal.

9. Method according to claim 8, wherein said step of treating is by oral administration.

10. Method according to claim 8, wherein said steps of applying are by oral administration.

11. Method according to claim 10, wherein curcumin is orally administered in an amount of 0.8 g/kg body weight of said living animal.

12. Composition for performing the method according to claim 1, comprising an organic and/or an inorganic salt selected from the group consisting of lithium, beryllium, magnesium, calcium, aluminum, and ammonium salts, and mixtures thereof, to remove bacteria.

13. Composition for performing the method according to claim 1, comprising erythrosine and/or anti-oxidants to remove bacteria.

14. Composition for performing the method according to claim 1, comprising curcumin or a derivative thereof as an adhesion stimulating substance.

15. Composition according to claim 10, comprising curcumin in the form of oleo-resins or plant extracts including curcumin and turmenic acid.

16. Composition for performing the method according to claim 1, in the form of an ointment, cream or bathing liquid.

17. Composition for performing the method according to claim 1 in the form of a dentifrice comprising at least one organic and/or inorganic salt of lithium, beryllium, magnesium, calcium, ammonium, or aluminum.

18. A process for promoting the adhesion of a desired bacteria to an interfacial surface, comprising applying to said surface an effective amount of an adhesion promoting substance comprising curcumin or a derivative thereof, and applying to said surface fimbriated desired bacteria.

* * * * *